United States Patent [19]

Oliver

[11] Patent Number: 5,344,955
[45] Date of Patent: Sep. 6, 1994

[54] PREPARATION OF 1-AMINO-CYAN-AMIDO-2,2-DICYANO-ETHYLENE, SODIUM SALT

[75] Inventor: Ward H. Oliver, Baton Rouge, La.

[73] Assignee: Ciba-Geigy Corporation, Ardsley, N.Y.

[21] Appl. No.: 97,098

[22] Filed: Jul. 26, 1993

Related U.S. Application Data

[63] Continuation of Ser. No. 19,521, Feb. 19, 1993, abandoned.

[51] Int. Cl.$^5$ ............................................. C07C 253/30
[52] U.S. Cl. ..................................... 558/375; 558/453
[58] Field of Search ................................ 558/375, 453

[56] References Cited

U.S. PATENT DOCUMENTS 4,783,468 11/1988 Kristinsson et al. ................ 514/275

OTHER PUBLICATIONS

The Chemistry of the Cyano Group; Edited by Zvi Rappoport (1970); pp. 546–547; Interscience Publishers.
Chem. Ber., 101; pp. 1232–1243; (1968); Allenstein, et al.
Chem. Ber., 101; pp. 1244–1249; (1968); Allenstein, et al.
J. Org. Chem.; 27; pp. 433–438; (1962); Trofimenko, et al.
J. Chem. Soc.; (1948); pp. 1630–1636; Curd, et al.

*Primary Examiner*—Joseph Paul Brust
*Attorney, Agent, or Firm*—Kevin T. Mansfield

[57] ABSTRACT

1-Amino-1-cyanamido-2,2-dicyanoethylene, sodium salt is prepared by a process which comprises reacting malononitrile with sodium dicyanamide at an elevated temperature and in the presence of an aprotic, dipolar solvent. The subject compound is useful as an intermediate to prepare substituted pyrimidines.

15 Claims, No Drawings

PREPARATION OF 1-AMINO-CYAN-AMIDO-2,2-DICYANOETHYLENE, SODIUM SALT

This application is a continuation of application Ser. No. 08/019,521, filed Feb. 19, 1993, now abandoned.

The present invention relates to a novel process for the preparation of 1-amino-1-cyanamido-2,2-dicyanoethylene, sodium salt of the formula

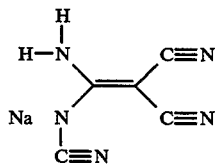

U.S. Pat. No. 4,783,468 discloses that 2-chloro-4,6-diamino-5-cyanopyrimidine is a valuable intermediate in the preparation of certain substituted 2,4-diamino-5-cyanopyrimidines that are useful as pesticides. Chem. Ber. 101, 1968, 1244–1249, teaches that this intermediate may be synthesized in high yield by treating a slurry of 1-amino-1-cyanamido-2,2-dicyanoethylene, sodium salt with excess hydrogen chloride in absolute ether. However this sodium salt precursor is only obtained in a modest yield of 28% by reaction of sodium cyanamide with 1-amino-1-ethoxy-2,2-dicyanoethylene (Chem. Ber. 101, 1968, 1232–1241), and this latter compound itself is several steps removed from readily available starting materials.

The number of steps and the low overall yield make the above process for the preparation of 1-amino-1-cyanamido-2,2-dicyanoethylene, sodium salt expensive and commercially unattractive. Thus there is a need for an improved process for the preparation of 1-amino-1-cyanamido-2,2-dicyanoethylene, sodium salt from readily available starting materials which would have fewer steps and afford a higher overall yield.

There has now been found a novel process by which 1-amino-1-cyanamido-2,2-dicyanoethylene, sodium salt can be prepared in good quality and yield in a single step from readily available starting materials. The present invention thus comprises a process for the preparation of 1-amino-1-cyanamido-2,2-dicyanoethylene, sodium salt which comprises reacting malononitrile with sodium dicyanamide at an elevated temperature and in the presence of an aprotic, dipolar solvent.

The reaction of malononitrile with sodium dicyanamide to give the title compound is preferably carried out at a temperature in the range of 120°–200° C., especially in the range of 130°–180° C. and most especially in the range of 140°–155° C. Conveniently the reaction is carried out at the reflux temperature of the mixture at atmospheric pressure. However it may be carried out at reduced or elevated pressure if desired. Depending on the temperature, the reaction will be complete in from 10 minutes to 4 hours. The reaction time is not critical since the product has good stability under the reaction conditions.

Preferred solvents for the reaction are N,N-di($C_1$-$C_4$alkyl)amides such as dimethylformamide and dimethylacetamide, N-($C_1$-$C_4$alkyl)$C_4$-$C_5$cyclic amides such as N-methylpyrrolidone and open chain or cyclic ureas such as tetramethylurea, N,N-dimethylethyleneurea and N,N-dimethylpropyleneurea. Sulfoxides and sulfones such as dimethylsulfoxide and sulfolane can also be used.

The amount of solvent is not critical but should at least be enough to ensure good mixing. Use of larger amounts gives a slight yield increase but results in increased solvent recovery costs and decreased output per batch. Generally the weight of the solvent should at least be equal to the weight of the two reactants. Preferably it is 1.5 to 4 times the weight of the two reactants and most preferably it is 2 to 3 times their weight.

The two reactants are commercially available and are generally employed in about stoichiometric amounts. While the sodium salt of dicyanamide is normally used because of availability and cost, analogous results are obtained with the corresponding lithium and potassium dicyanamides.

The order of addition is not critical. The two reactants may be added to the solvent prior to heating, or one may be added, with or without a solvent, to a heated solution of the other.

If desired, the product may be isolated from the reaction mixture by adding an organic solvent in which the product has poor solubility, causing the product to precipitate as a crystalline solid. Alcohols and esters, preferably those boiling below about 150° C. for ease of recovery, are illustrative of preferred solvents for this purpose. Optionally a part of the reaction solvent may be removed under reduced pressure prior to addition of the organic solvent in which the product has poor solubility. The crystals may be collected by filtration and dried or further purified by recrystallization or trituration, again using an organic solvent in which the product has poor solubility.

The filtered and washed product is typically 80–95% pure and is usually obtained in 55–80% yield. It is a white to dark yellow crystalline solid which darkens above 300° C. and melts above 360° C. Its infrared spectrum conforms to that published (Chem. Ber. 101, 1968, 1241).

The following non-limiting examples illustrate the present invention.

EXAMPLE 1

To a 250 ml flask is charged 6.6 gm (0.1 mole) of malononitrile, 8.9 gm (0.1 mole) of sodium dicyanamide and 40 ml of dimethyl formamide. The stirred mixture is heated to reflux (168° C.) and held 15 minutes; then cooled to about room temperature. Then 150 ml 2-butanol is added and the stirred mixture is cooled in an ice bath. The solids are filtered, washed with 2-butanol and dried overnight in a vacuum oven. There is obtained 11.4 gm of 1-amino-1-cyanamido-2,2-dicyanoethylene, sodium salt, 81.2% pure, or a 59.7% yield.

EXAMPLE 2

To a 250 ml flask is charged 6.6 gm (0.1 mole) of malononitrile, 8.9 gm (0.1 mole) of sodium dicyanamide and 40 ml of N-methylpyrrolidone. The stirred mixture is heated to 145° C. and held for one hour, then cooled to about room temperature. Then 150 ml of 2-butanol is added and the stirred mixture is cooled in an ice bath. The solids are filtered, washed with 2-butanol and dried. There is obtained 10.7 gm of 1-amino-1-cyanamido-2,2-dicyanoethylene, sodium salt, 82.5% pure, or a 57.0% yield.

EXAMPLE 3

To a 250 ml flask is charged 6.6 gm (0.1 mole) of malononitrile, 8.9 gm (0.1 mole) of sodium dicyanamide and 40 ml of dimethyl sulfoxide. The stirred mixture is heated to 140° C. and held for 1.5 hours; then cooled to about room temperature. Then 150 ml 2-butanol is added and the stirred mixture is cooled in an ice bath. The solids are filtered, washed with 2-butanol and dried. There is obtained 12.6 gm of 1-amino-1-cyanamido-2,2-dicyanoethylene, sodium salt, 72.3% pure or a 58.8% yield.

EXAMPLE 4

To a 500 ml flask is charged 22.5 gm (0.25 mole) of sodium dicyanamide, 300 ml of N,N-dimethylacetamide and 16.5 gm (0.25 mole) of malononitrile. The stirred mixture is heated to 146° C. and a sufficient vacuum is applied to cause the N,N-dimethylacetamide to begin to distill. Vacuum distillation is continued at 146°–147° C. until about 260 ml has been collected. Then to the remaining slurry is charged 400 ml of 2-butanol and the slurry is stirred in an ice bath for one hour. The solids are collected by filtration and washed with 2-butanol. The dried product amounts to 35.6 gm of 1-amino-1-cyanamido-2,2-dicyanoethylene, sodium salt, 80.8% pure or a 74.4% yield.

EXAMPLE 5

To a 250 ml flask is charged 18.5 gm (0.21 mole) of sodium dicyanamide and 70 ml of N,N-dimethylacetamide. The stirred mixture is heated to 160° C. and a solution of 13.2 gm (0.20 mole) of malononitrile in 10 ml of N,N-dimethylacetamide is added dropwise over 10 minutes. The mixture is stirred at 160° C. for 15 minutes; then cooled and the slurry added to 350 ml of ethyl acetate. The slurry is stirred for 45 minutes. Then the solids are collected by filtration and washed with ethyl acetate. The dried product amounts to 20.7 gm of 1-amino-1-cyanamido-2,2-dicyanoethylene, sodium salt, 93.3% pure or a 62.5% yield.

EXAMPLE 6

To a 1 liter flask is charged 89 gm( 1.0 mole) of sodium dicyanamide and 282 ml of N,N-dimethylacetamide. The stirred mixture is heated to 147° C. and 72.6 gm (1.1 mole) of malononitrile in 72.6 gm of N,N-dimethylacetamide is added dropwise over 2 hours and 25 minutes. The mixture is stirred at 147° C. for an additional 3 hours and 15 minutes; then cooled to 60° C. Next the reaction mixture is charged to a 2 liter flask containing 1276 gm of 2-butanol and stirred overnight at room temperature. The slurry is then filtered, and the wet cake slurried in 319 gm 2-butanol and again filtered. The solids are dried overnight at 70° C. in a vacuum oven. There is obtained 144.9 gm of 1-amino-1-cyanamido-2,2-dicyanoethylene, sodium salt, 84.5% pure, or a 78.9% yield.

EXAMPLE 7

To a 500 ml flask is charged 13.2 gm (0.2 mole) of malononitrile, 18.2 gm (0.2 mole) of sodium dicyanamide and 80 ml of tetramethylurea. The stirred mixture is heated at 145° C. for 2.5 hours; then cooled to about room temperature. The slurry is diluted with 300 ml 2-butanol and stirred in an ice bath for one hour. The solids are filtered, washed with 50 ml of 2-butanol. The product is dried overnight at 70° C. in a vacuum oven to yield 25.0 gm of 1-amino-1-cyanamido-2,2-dicyanoethylene, sodium salt, 80.7% pure or a 65.0% yield.

What is claimed is:

1. A process for the preparation of 1-amino-1-cyanamido-2,2-dicyanoethylene, sodium salt which comprises reacting malononitrile with sodium dicyanamide at an elevated temperature and in the presence of an aprotic, dipolar solvent.

2. A process according to claim 1, wherein the temperature is in the range of 120°–200° C.

3. A process according to claim 2, wherein the temperature is in the range of 130°–180° C.

4. A process according to claim 3, wherein the temperature is in the range of 140°–155° C.

5. A process according to claim 1, wherein the solvent is a N,N-di($C_1$–$C_4$alkyl)amide, an N-($C_1$–$C_4$alkyl)-$C_4$–$C_5$cyclic amide, an open chain or cyclic urea, a sulfoxide or a sulfone.

6. A process according to claim 4, wherein the solvent is selected from dimethylformamide, dimethylacetamide, N-methylpyrrolidone, tetramethylurea, N,N-dimethylethyleneurea, N,N-dimethylpropyleneurea and dimethylsulfoxide.

7. A process according to claim 1, wherein the weight of the solvent is 1.5 to 4 times the weight of the two reactants.

8. A process according to claim 7, wherein the weight of the solvent is 2 to 3 times the weight of the two reactants.

9. A process according to claim 1, which is carried out at the reflux temperature of the mixture at atmospheric pressure.

10. A process according to claim 1, wherein the two reactants are added to the solvent prior to heating the mixture to the reaction temperature.

11. A process according to claim 1, wherein one of the reactants is added, with or without a solvent, to a heated solution containing the other reactant.

12. A process according to claim 11, wherein the reactant which is added to a heated solution containing the other reactant is dissolved in a solvent.

13. A process according to claim 1, wherein the product, 1-amino-1-cyanamido-2,2-dicyanoethylene, sodium salt, is precipitated from the reaction mixture by adding thereto an organic solvent in which the product has poor solubility.

14. A process according to claim 13, wherein the organic solvent in which the product has poor solubility is an alcohol or an ester.

15. A process according to claim 13, wherein a part of the reaction solvent is distilled off and then the solvent in which the product has poor solubility is added to the reaction mixture.

* * * * *